US009903786B2

(12) United States Patent
Taguchi et al.

(10) Patent No.: US 9,903,786 B2
(45) Date of Patent: Feb. 27, 2018

(54) RADIAL ROLLING-BEARING TESTING DEVICE

(71) Applicant: NSK LTD., Tokyo (JP)

(72) Inventors: Ikuo Taguchi, Fujisawa (JP); Masato Yoshida, Fujisawa (JP)

(73) Assignee: NSK LTD., Tokyo (JP)

( * ) Notice: Subject to any disclaimer, the term of this patent is extended or adjusted under 35 U.S.C. 154(b) by 376 days.

(21) Appl. No.: 14/781,954

(22) PCT Filed: Apr. 4, 2014

(86) PCT No.: PCT/JP2014/060003
§ 371 (c)(1),
(2) Date: Oct. 2, 2015

(87) PCT Pub. No.: WO2014/163193
PCT Pub. Date: Oct. 9, 2014

(65) Prior Publication Data
US 2016/0033361 A1 Feb. 4, 2016

(30) Foreign Application Priority Data

Apr. 5, 2013 (JP) .................................. 2013-079789
Apr. 5, 2013 (JP) .................................. 2013-079790

(51) Int. Cl.
*G01M 13/04* (2006.01)
*G01N 19/00* (2006.01)

(52) U.S. Cl.
CPC .......... *G01M 13/04* (2013.01); *G01M 13/045* (2013.01); *G01N 19/00* (2013.01)

(58) Field of Classification Search
CPC ..... G01M 13/04; G01M 13/045; G01N 19/00
(Continued)

(56) References Cited

U.S. PATENT DOCUMENTS 5,298,323 A   3/1994 Narai et al.
6,550,258 B1* 4/2003 Shoulders ............... F04C 28/06
                                                           62/472
(Continued)

FOREIGN PATENT DOCUMENTS

JP    61-163946 U    10/1986
JP    H 7-35144 A    2/1995
(Continued)

OTHER PUBLICATIONS

Communication dated Mar. 23, 2016, issued by the European Patent Office in counterpart European Patent Application No. 14779473.9.
(Continued)

*Primary Examiner* — Hezron E Williams
*Assistant Examiner* — Tarun Sinha
(74) *Attorney, Agent, or Firm* — Sughrue Mion, PLLC

(57) ABSTRACT

A radial rolling-bearing testing device includes a rotary shaft which an inner ring of a radial rolling bearing is fitted, a rotational driving section which rotates a rotary shaft, a lubricant reservoir which is configured so as to retain lubricant in which a portion of the radial rolling bearing is immersed, and a load applying section which is configured so as to apply a radial load to the radial rolling bearing. A bottom surface of the lubricant reservoir is a curved concave surface which has a partially cylindrical form which is concentric to a central axis of the rotary shaft. An entirety of a housing which supports the rotary shaft may be integrally formed.

8 Claims, 8 Drawing Sheets

(58) Field of Classification Search
USPC .............................................................. 73/9
See application file for complete search history.

(56) References Cited

U.S. PATENT DOCUMENTS

2011/0273064 A1* 11/2011 Vuolle-Apiala ....... H02K 7/116
310/75 R
2014/0007657 A1* 1/2014 Matsubara ............ G01M 13/04
73/53.05

FOREIGN PATENT DOCUMENTS

| | | |
|---|---|---|
| JP | 8-141380 A | 6/1996 |
| JP | 8-166017 A | 6/1996 |
| JP | H 9-32525 A | 2/1997 |
| JP | 3018355 A | 3/2000 |
| JP | 3448998 B2 | 9/2003 |
| JP | 2005-106479 A | 4/2005 |
| JP | 2007-003196 A | 1/2007 |
| WO | 2012/117970 A1 | 9/2012 |

OTHER PUBLICATIONS

Office Action dated Dec. 21, 2016, issued by the Korean Intellectual Property Office in counterpart Korean Application No. 10-2015-7027077.
Communication dated Apr. 5, 2017, from the State Intellectual Property Office of People's Republic of China in counterpart Application No. 201480020060.8.
International Search Report for PCT/JP2014/060003 dated Jun. 24, 2014 [PCT/ISA/210].
Written Opinion for PCT/JP2014/060003 dated Jun. 24, 2014 [PCT/ISA/237].

* cited by examiner

RADIAL ROLLING-BEARING TESTING DEVICE

TECHNICAL FIELD

The present invention relates to a radial rolling-bearing testing device for performing durability evaluation of a radial rolling bearing which is installed on a rotation support section of a vehicle, various machine tools, various industrial machines, and the like.

BACKGROUND ART

A life of a rolling bearing varies due to a variety of complexly intertwined factors such as a material, a form, a size, a lubricant state, and a load of a bearing ring or a rolling element of the rolling bearing. Accordingly, in order to obtain the rolling bearing which has an appropriate durability according to use, it is necessary to perform a testing in order to know effects which the various factors exert on the life of the rolling bearing. FIG. 7 illustrates a radial rolling-bearing testing device in an example of the related art (for example, refer to Patent Document 1). In the radial rolling-bearing testing device, a leading end section (the left end section in FIG. 7) and a portion near to a base end of a rotary shaft 2 are rotatably supported inside a fixed housing 1 by a pair of radial rolling bearings 3 and 3 which each are bearings to be tested. A movable housing 4 is disposed concentrically to the rotary shaft 2 in a periphery of a center section of the rotary shaft 2 which is positioned between the radial rolling bearings 3 and 3. The movable housing 4 is provided inside the fixed housing 1 in a state in which a displacement in the radial direction is possible and a displacement in a rotation direction is prevented. Then, a support bearing 5 is provided between an inner peripheral surface of the movable housing 4 and an outer peripheral surface at the center section of the rotary shaft 2. Then, lower half sections of the support bearing 5 and the radial rolling bearings 3 and 3 are immersed in lubricant which is retained in a lubricant reservoir 6 that is provided inside the fixed housing 1. According to the need, foreign matters 7 and 7 such as metal powders and ceramic powders are mixed into the lubricant. A radial load F with a desired value which faces a vertical direction (up-and-down direction in FIG. 7) is freely applied to the movable housing 4 by a pressurizing device such as a hydraulic cylinder.

In a case where a life testing of the radial rolling bearings 3 and 3 is performed, the radial rolling bearings 3 and 3 are pressed in the vertical direction via the movable housing 4, the support bearing 5, and the rotary shaft 2 by pressing the movable housing 4 using the pressurizing device, and the rotary shaft 2 is driven so as to rotate. As a result, the life testing for durability evaluation of the radial rolling bearings 3 and 3 can be performed in a state in which the desired radial load F is applied and rotated at the desired rotation speed. In a case where the life testing of the radial rolling bearings 3 and 3 is performed using such a radial rolling-bearing testing device as described above, it is important to secure a circulation of the lubricant inside the lubricant reservoir 6, and uniformize characteristics such as an oil temperature of lubricant inside an entirety of lubricant reservoir 6.

Here, in a case of such a radial rolling-bearing testing device as described above, in order that the evaluation is performed with high reliability, it is important to sufficiently increase a rigidity of the fixed housing 1. That is, in a case where the rigidity of the fixed housing 1 is insufficient, there is a possibility that a portion of the fixed housing 1 which supports the radial load F deforms (elastically deforms). Thereby, there is a possibility that it is not possible to normally apply the radial load F to the radial rolling bearings 3 and 3 which are bearings to be tested, and a variance of test results is increased.

FIG. 8 illustrates a radial rolling-bearing testing device in a second example of the related art. In a fixed housing 1a with a rectangular box form which is open upward, a pair of side plate sections 9 and 9 which are parallel to each other, and a pair of end plate sections which connect end sections of the side plate sections 9 and 9 are formed so as to be supportedly fixed to an end plate section 8 with a flat plate form by respective welds and the like. When the life testing of the radial rolling bearing 3a is performed by the radial rolling-bearing testing device which includes with the fixed housing 1a, according to rotations (revolutions) of balls 10 and 10 of the radial rolling bearing 3a, the lubricant inside the lubricant reservoir 6a, which is provided inside the fixed housing 1a, is caused to flow in a same direction as a rotation direction of each of the balls 10 and 10. In the case of the second example of the related art, it is easy for the lubricant to be stagnated at corner sections (portions which are enclosed by a dotted line a in FIG. 8) close to a boundary of an upper surface of the bottom plate section 8 and an inner side surfaces of the side plate sections 9 and 9. As a result, there is a possibility that properties of the lubricant are not uniformized inside the lubricant reservoir 6a. In particular, in a case where the foreign matters 7 and 7 are mixed into the lubricant, there is a possibility that the testing is not performed with high reliability since the foreign matters 7 and 7 are stagnated in the corner sections, and it is not possible to appropriately feed the foreign matters 7 and 7 to the load zone of the radial rolling bearing 3a which is a bearing to be tested.

PRIOR ART DOCUMENT

Patent Document

Patent Document 1: JP-A-2007-003196

SUMMARY OF THE INVENTION

Problem to be Solved

The present invention has an object of providing a radial rolling-bearing testing device which performs a testing with high reliability.

Means for Solving the Problem

A radial rolling-bearing testing device of the present invention is used in order to perform durability evaluation (life testing) of a radial rolling bearing. The radial rolling bearing which is the target for a life testing includes an outer ring, an inner ring, and a plurality of rolling elements. The outer ring has an inner peripheral surface on which an outer ring raceway is formed. The inner ring has an outer peripheral surface on which an inner ring raceway is formed. The rolling elements are provided so as to freely rotate between an outer ring raceway and an inner ring raceway.

According to an aspect of the present invention, the radial rolling-bearing testing device includes a rotary shaft, a lubricant reservoir, a rotational driving section, and a load applying section. The inner ring of the radial rolling bearing, which is bearing to be tested, is fitted around an outside of the rotary shaft. The rotational driving section is configured such that the rotary shaft is driven so as to rotate. The lubricant reservoir is configured such that lubricant which immerses a portion of the radial rolling bearing is retained. The load applying section is configured so as to apply the radial load to the radial rolling bearing.

A bottom surface of the lubricant reservoir is a curved concave surface with a partially cylindrical form which is concentric to a central axis of the rotary shaft (a central axis of the radial rolling bearing). A radius of a curvature of the bottom surface of the lubricant reservoir is preferably 0.6 times or more and 2 times or less than an outer diameter of the radial rolling bearing, and is more preferably equal to or less than the outer diameter of the radial rolling bearing. In a state before the rotary shaft is driven so as to rotate, an oil level (upper surface) of the lubricant may be positioned on the central axis of the rotary shaft.

The radial rolling-bearing testing device may further include a heater which is configured so as to maintain an oil temperature of the lubricant at a desired temperature, and a support a sleeve which the radial rolling bearing is fitted around an inside. The heater is provided between a bottom surface of the lubricant reservoir and an outer peripheral surface of the support sleeve. The heater is provided in a state in which a gap is interposed between a lower surface of the heater and the bottom surface of the lubricant reservoir, and between a upper surface of the heater and the outer peripheral surface of the support sleeve. The heater may be curved along the bottom surface of the lubricant reservoir.

A foreign matter such as metal powder and ceramic powder may be mixed into the lubricant. The load applying section applies the radial load in a horizontal direction.

According to another aspect of the present invention, a radial rolling-bearing testing device includes a housing, a rotary shaft, a rotational driving section, and a load applying section. The rotary shaft is supported inside the housing so as to freely rotate, and an inner ring of the radial rolling bearing is fitted around the outside. The rotational driving section is configured such that the rotary shaft is driven so as to rotate. The load applying section is configured so as to apply the radial load to the radial rolling bearing.

An entirety of the housing is integrally formed without being configured to connect (fix) a plurality of members. The housing is, for example, a carbon steel. The housing is formed by carrying out forging on a carbon steel material, and furthermore as necessary, carrying out machining.

A lubricant reservoir, which is configured so as to retain lubricant that immerses a portion of the radial rolling bearing, may be provided inside the housing. The load applying section may apply the radial load in a horizontal direction. A bottom surface of the lubricant reservoir may have a curved concave surface with a partially cylindrical form that is concentric to a central axis of the rotary shaft. A radius of a curvature of the bottom surface of the lubricant reservoir is preferably 0.6 times or more and 2 times or less than an outer diameter of the radial rolling bearing, and is more preferably equal to or less than the outer diameter of the radial rolling bearing. A foreign matter such as metal powder and ceramic powder may be mixed into the lubricant.

Effects of Invention

According to the testing device described above, since the bottom surface of the lubricant reservoir which retains lubricant with a curved concave surface which has a partially cylindrical form that is concentric to the central axis of the rotary shaft, it is possible to prevent the lubricant from stagnating inside the lubricant reservoir. For this reason, it is possible to circulate the lubricant. Accordingly, it is possible to uniformize properties of the lubricant inside an entirety of the lubricant reservoir. Thereby, it is possible to perform an evaluation with high reliability in relation to the life of the radial rolling bearing.

According to the testing device described above, since the entirety of the housing is integrally formed, it is possible to sufficiently increase a rigidity of the housing, and it is possible to normally apply the radial load to the radial rolling bearing which is a bearing to be tested. As a result, it is possible to suppress a variation of testing results, and perform an evaluation with high reliability in relation to the life of the radial rolling bearing.

DESCRIPTION OF EMBODIMENTS

Figure 1:
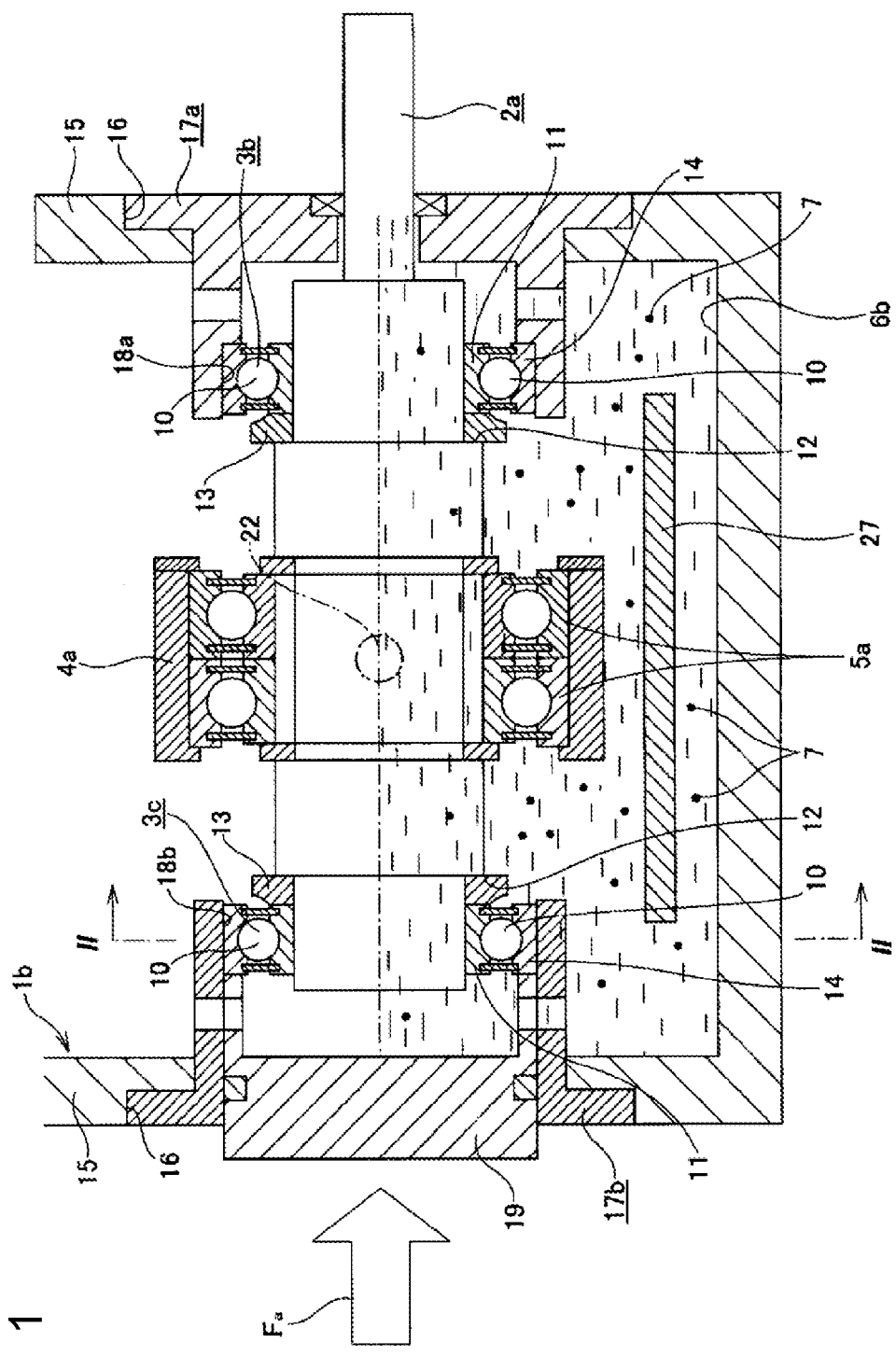
FIG. 1 is a sectional view of a radial rolling-bearing testing device in an embodiment of the present invention.

FIGS. 1 to 3B illustrate a radial rolling-bearing testing device in an embodiment of the present invention. As shown in FIG. 1, a leading end section and a portion near to a base end of a rotary shaft 2a are rotatably supported inside a fixed housing 1b by a pair of radial rolling bearings 3b and 3c which each are bearings to be tested. That is, inner rings 11 and 11 of the radial rolling bearings 3b and 3c are fitted around an outside of the leading end section and a portion near to the base end of the rotary shaft 2a. Inner side surfaces of the inner rings 11 and 11 abut against step sections 12 and 12 which are provided in a center section of the rotary shaft 2a via washers 13 and 13. Outer rings 14 and 14 of the radial rolling bearings 3b and 3c are supported on a pair of axial side wall sections 15 and 15 of the fixed housing 1b which are erected in a vertical direction in a state of being separated in an axial direction of the rotary shaft 2a. Support sleeves 17a and 17b with substantially cylindrical forms are attached to an inside of circular holes 16 and 16 which are provided in the axial side wall sections 15 and 15. Then, the outer rings 14 and 14 are respectively fitted around an inside of support sections 18a and 18b with cylindrical forms which are provided on an inner peripheral surface of leading end sections of the support sleeves 17a and 17b. An outer side surface of the outer ring 14 of the radial rolling bearing 3b abuts against a stepped surface which is provided at a back end section of the support section 18a of the support sleeve 17a. Thereby, the radial rolling bearing 3b is firmly held in the axial direction between an outer side surface of the washer 13 and the stepped surface of the support section 18a of the support sleeve 17a. In contrast to this, an outer side surface of the outer ring 14 of the other radial rolling bearing 3c abuts against the a leading end surface of a piston section 19 which is inserted (fitted) into an inside of the other support sleeve 17b displaceably in the axial direction. Thereby, the radial rolling bearing 3c is firmly held in the axial direction between an outer side surface of the washer 13 and the leading end surface of the piston section 19. In the case of the present example, it is possible to apply an axial load Fa with a desired value to the radial rolling bearings 3b and 3c by pressing a base end surface of the piston section 19 using a pressurizing device such as a hydraulic cylinder which is not shown in the drawings.

A movable housing 4a with a substantially cylindrical form is disposed concentrically to the rotary shaft 2a on a periphery of the center section of the rotary shaft 2a. Then, a pair of support bearings 5a and 5a are provided between an inner peripheral surface of the movable housing 4a and an outer peripheral surface at the center section of the rotary shaft 2a. The movable housing 4a is provided inside the fixed housing 1b in a state in which a displacement in the radial direction is possible and a displacement in the rotation direction is prevented. In the case of the present example, it is possible to apply a radial load Fr with a desired value to the movable housing 4a in the horizontal direction. That is, a leading end section of a pressing jig 22 with a substantially cylindrical form is inserted into a through hole 21 which is provided in a state of passing through a width direction side wall section 20a in the horizontal direction, out of a pair of width direction side wall sections 20a and 20b to which each of end sections of the axial side wall sections 15 and 15 of the fixed housing 1b are connected, a base end surface (a right end surface in FIG. 2) of a pressing jig 22 is abutted by a leading end surface (a left end surface in FIG. 2) of a pressing rod 23 of a pressurizing device, which is installed outside the fixed housing 1b (the width direction side wall section 20a), such as a hydraulic cylinder via a steel ball 24 and a pressing plate 25, and a radial load applying section is configured. A vibration of the radial rolling bearings 3b and 3c is freely detected via each of members 2a, 5a, 4a, and 22 by providing a vibration sensor 26 on an outer side surface of the pressing plate 25 and detecting a vibration of the pressing plate 25 using the vibration sensor 26.

The rotary shaft 2a is connected to an output shaft of a driving source such as an electric motor directly or via a pulley and a coupling that are spanned by an endless belt, and a rotational driving section for driving the rotary shaft 2a so as to rotate at a desired rotation speed is configured.

Figure 3A:
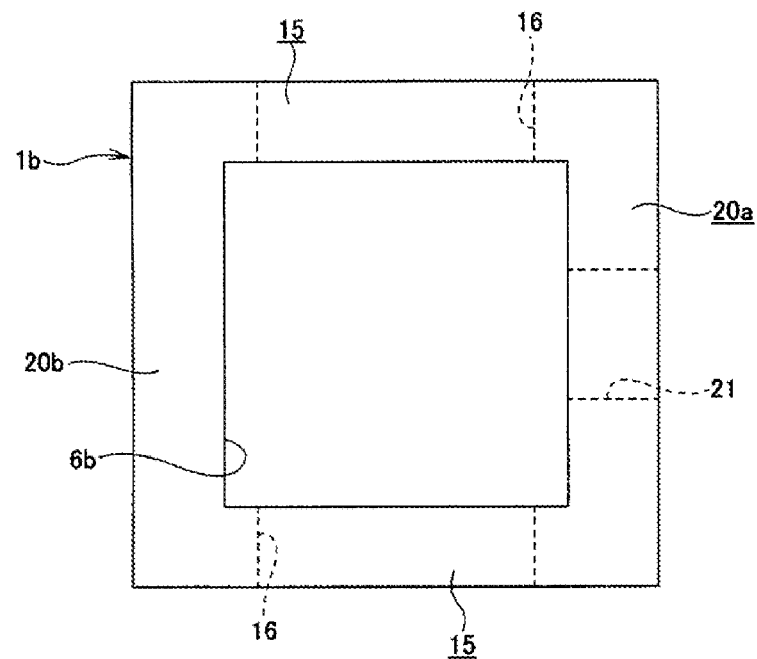
FIG. 3A is a planar view of a fixed housing.
Figure 3B:
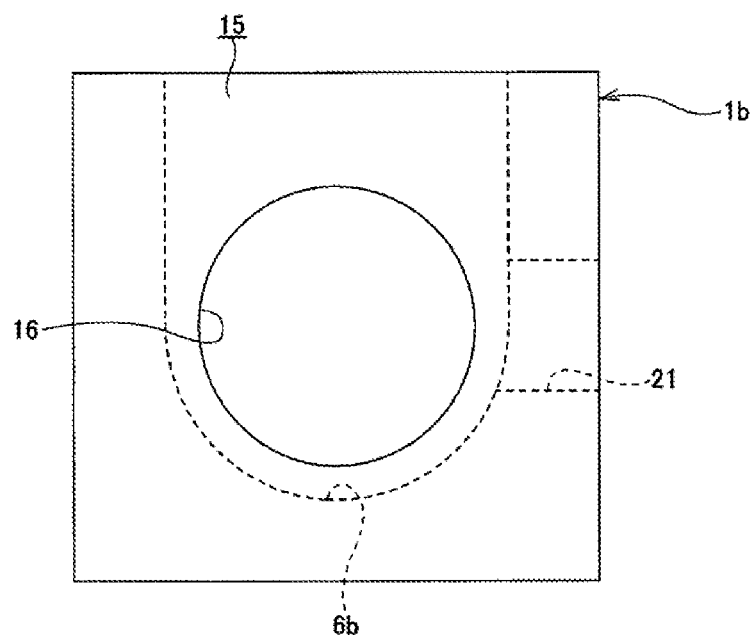
FIG. 3B is a side surface view of the fixed housing.

In the case of the present example, as shown in FIG. 3A, an entirety of the fixed housing 1b is integrally formed in a substantially rectangular box form which is open upward, by carrying out forging and machining on a carbon steel material. A lubricant reservoir 6b is provided inside the fixed housing 1b, and a bottom surface of the lubricant reservoir 6b is a curved concave surface with a partial cylindrical form which is concentric to the rotary shaft 2a. A radius of a curvature r of the bottom surface of the lubricant reservoir 6b is 0.6 times or more and 2 times or less than an outer diameter D of the radial rolling bearings 3b and 3c ($0.6D \leq r \leq 2D$), and is preferably equal to or less than the outer diameter D. A heater 27 is provided on a bottom section of the lubricant reservoir 6b which is normally immersed in lubricant. In detail, the heater 27 with a plate form is provided between the bottom surface of the lubricant reservoir 6b and outer peripheral surfaces of the movable housing 4a and the support sleeves 17a and 17b. A gap is interposed between a lower surface of the heater 27 and the bottom surface of the lubricant reservoir 6b, and between a upper surface of the heater 27 and the outer peripheral surfaces of the movable housing 4a and the support sleeves 17a and 17b. The heater 27 is curved along the bottom surface of the lubricant reservoir 6b. That is, the upper and lower surfaces of the heater 27 are set as a curved surface with a partial cylindrical form which is concentric to the central axis of the rotary shaft 2a.

The lubricant, into which foreign matters 7 and 7 such as metal powders and ceramic powders are mixed at a desired ratio, is retained in the lubricant reservoir 6b. For this reason, a mixing ratio of the foreign matters 7 and 7 in the lubricant does not vary from a start of an actual testing to an end of the actual testing. Then, the lubricant is stirred according to rotations of the rotary shaft 2a, the radial rolling bearings 3a and 3b, and the support bearings 5a and 5b, and the foreign matters 7 and 7 are uniformly dispersed within the lubricant. A rectifying means for making a lubricant flow inside the lubricant reservoir 6b appropriate may be provided inside the lubricant reservoir 6b.

In a case where the durability testing (life testing) of the radial rolling bearings 3b and 3c which are bearings to be tested is performed by the radial rolling-bearing testing device described above, taking a stirring effect by the rotary shaft 2a and lubricity of a load zone into consideration, it is preferable to regulate the lubricant inside the lubricant reservoir 6b within a range from a lower end section to an upper end section of the rotary shaft 2a in a state before the rotary shaft 2a is driven so as to rotate. That is, when an oil level (upper surface) of the lubricant is set below the lower end section of the rotary shaft 2a, the stirring effect by the rotary shaft 2a cannot be obtained, and when the oil level (upper surface) of the lubricant is set above the upper end section of the rotary shaft 2a, a large portion of the load zone is immersed in the lubricant, it becomes difficult for effects of the foreign matters to be noticed, and the testing time increases. Therefore, in the case of the present example, the oil level of the lubricant is retained so as to be positioned on the central axis of the rotary shaft 2a. Then, in the state before the rotary shaft 2a is driven so as to rotate, only the lower half sections of the radial rolling bearings 3b and 3c are immersed in the lubricant. Thereby, during the life testing, there is a state in which at least a lower end section of the outer peripheral surface of the rotary shaft 2a is immersed in the lubricant, and portions of at least one third from the lower ends of the radial rolling bearings 3b and 3c are immersed in the lubricant in the radial direction. Then, an oil temperature of the lubricant is maintained at a desired temperature (for example, 100° C.) by the heater 27. In the case of the present example, since the oil level of the lubricant is positioned on the central axis of the rotary shaft 2a in the state before the rotary shaft 2a is driven so as to rotate, also during the life testing, the rotary shaft 2a and the radial rolling bearings 3b and 3c are easily maintained within a predetermined temperature range. The rotary shaft 2a is pressed in the axial direction by pressing the base end surface of the piston section 19, and the desired axial load Fa is applied to the radial rolling bearings 3b and 3c. Furthermore, the rotary shaft 2a is pressed in the horizontal direction by pressing the outer peripheral surface of the movable housing 4a using the pressing rod 23, and the desired radial load Fr is applied to the radial rolling bearings 3b and 3c. In this state, the rotary shaft 2a is driven so as to rotate at a desired rotation speed such that rotation (revolution) directions of balls 10 and 10 of the radial rolling bearings 3b and 3c are directions which pass the load zone (a portion illustrated by a thick line in FIG. 2), which is positioned in front of a direction in which the radial load Fr applies, from below to above (a clockwise direction in FIG. 2) in relation to a circumferential direction of the radial rolling bearings 3a and 3b. As a result, the radial rolling bearings 3b and 3c are driven so as to rotate at a desired rotation speed while the desired radial load Fr and axial load Fa are applied. In this state, at a point in time, when vibration values (amplitudes) of the radial rolling bearings 3b and 3c which are detected by the vibration sensor 26 exceed a threshold value that is set to equal or more than 1.5 times and less than 3 times (for example, 2 times) an initial vibration value at the start of the testing, is set as the life of the radial rolling bearings 3b and 3c, and the testing is completed. In a case where the threshold value is less than 1.5 times the initial vibration value, there is a possibility that the testing is completed due to the vibration based on a damage other than to the radial rolling bearings 3b and 3c. In a case where the threshold value is 3 or more times, there is a possibility that the damage progresses widely, and it is not possible to specify a part which is the origin of the damage. When replacing the radial rolling bearings 3b and 3c, in a state in which the support sleeves 17a and 17b are displaced outward in the axial direction, a replacement of the radial rolling bearings 3b and 3c is performed from both sides in the axial direction of the rotary shaft 2a.

Figure 6:
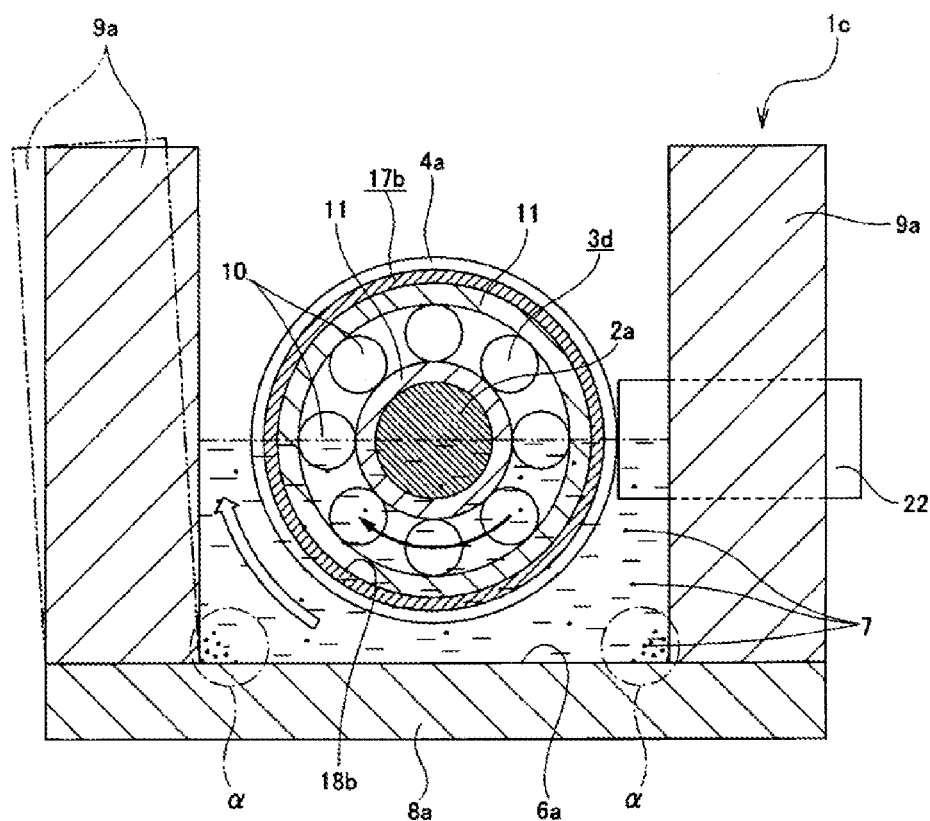
FIG. 6 is a view illustrating a comparative example for describing the effect of integrally forming the fixed housing.

According to the radial rolling-bearing testing device described above, in the life testing of the radial rolling bearings 3b and 3c, it is possible to prevent the lubricant from stagnating inside the lubricant reservoir 6b, and the properties of the lubricant are uniformized over an entirety of the inside of the lubricant reservoir 6b. That is, in the case of the present example, since the bottom surface of the lubricant reservoir 6b is set as a curved concave surface with a partial cylindrical form which is concentric to the central axis of the rotary shaft 2a, it is possible to prevent the lubricant and the foreign matters 7 and 7 having various large and small sizes which are mixed in the lubricant from stagnating (accumulating) in the lubricant reservoir 6b. That is, in a case of a structure of the comparative example which is illustrated in FIG. 6 described above, in the lubricant reservoir 6a which is provided inside a fixed housing 1c, the lubricant and the foreign matters 7 and 7 which are mixed in the lubricant easily stagnate at corner sections (portions which are enclosed by a dotted line a in FIG. 6) close to a boundary of an upper surface of the bottom plate section 8a and inside surfaces of the side plate sections 9a and 9a. In contrast to this, in a case of the present example, the lubricant and the foreign matters 7 and 7 are prevented from stagnating by setting the bottom surface of the lubricant reservoir 6b as a curved concave surface with a partial cylindrical form. When the lubricant reservoir 6b is cleaned, it is possible to prevent the foreign matters 7 and 7 from adhering to and remaining in the corner sections. Furthermore, in the case of the present example, the heater 27 between the bottom surface of the lubricant reservoir 6b and the outer peripheral surfaces of the movable housing 4a and the support sleeves 17a and 17b is provided in a state in which a gap is respectively interposed between each surface and the upper and lower surfaces of the heater 27. For this reason, it is possible to increase a flow speed of the lubricant at both of the upper and lower sides of the heater 27 based on a throttle of a flow path, and it is possible to make it more difficult for the lubricant and the foreign matters 7 and 7 to be stagnated. It is possible to perform a heat replacement with the lubricant with good efficiency. In particular, in the case of the present example, since the radius of the curvature r of the bottom surface of the lubricant reservoir 6a is 0.6 times or more and 2 times or less than the outer diameter D of the radial rolling bearings 3b and 3c (0.6D≤r≤2D), it is possible to enhance the circulation of the lubricant without increasing a required quantity of the lubricant. Furthermore, if the radius of the curvature r is equal to or less than the outer diameter D (r≤D), it is possible to reduce the quantity of the lubricant. That is, in a case where the radius of the curvature r is greater than 2 times the outer diameter D (r>2D), it is necessary to increase the quantity of the lubricant. Meanwhile, in a case where the radius of the curvature r is less than 0.6 times the outer diameter D (r<0.6D), the gaps at both of the upper and lower sides of the heater 27 are narrowed excessively, and the circulation of the lubricant is reduced. By providing the gaps at both of the upper and lower sides of the heater 27, it is possible to widen the contact area of the upper and lower surfaces of the heater 27 and the lubricant, and it is possible to adjust the temperature of the lubricant with good efficiency. Since the surface of the lubricant reservoir 6b is made to be smoothly continuous by setting the bottom surface of the lubricant reservoir 6b as a curved concave surface, the surface of the lubricant reservoir 6b is able to uniformly absorb or disperse a heat, and it is possible to prevent a temperature variance. In detail, it is possible to adjust the temperature of the lubricant, which is retained inside the lubricant reservoir 6a, within a desired temperature range of ±3° C.

In the case of the present example, only the lower half sections of the radial rolling bearings 3b and 3c are immersed in the lubricant, and the radial load Fr is applied to the radial rolling bearings 3b and 3c in the horizontal direction. Furthermore, the rotation direction of the rotary shaft 2a is regulated such that the balls 10 and 10 of the radial rolling bearings 3b and 3c are rotated (revolved) in a direction which passes the load zone from below to above.

For this reason, it is possible to set an appropriate state of the lubrication of the load zone which is positioned in front of the direction in which the radial load Fr applies, and it is possible to prevent an increasing of the variance of the testing results due to the lubricant in the load zone tending to be insufficient or depleted, and an increasing of a testing time due to the lubricant state being in excess. Furthermore, since the revolving direction of each of the balls 10 and 10 is regulated, it is also possible to appropriately feed the foreign matters 7 and 7, which are mixed in the lubricant that is retained inside the lubricant reservoir 6b, to the load zone, and from this perspective, the testing results are also made stable (the variance is suppressed).

Figure 2:
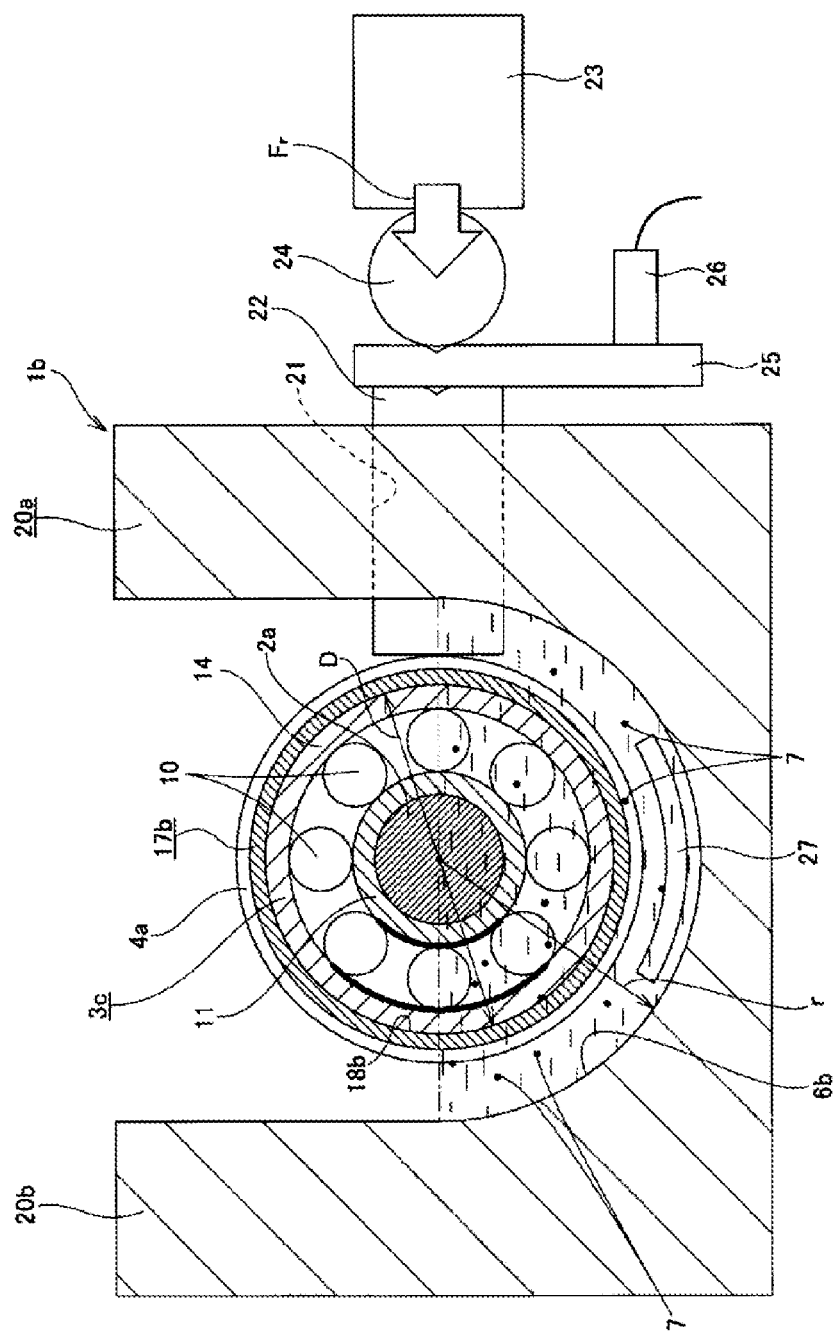
FIG. 2 is a schematic view including a sectional view along line II-II in FIG. 1.
Figure 4A:
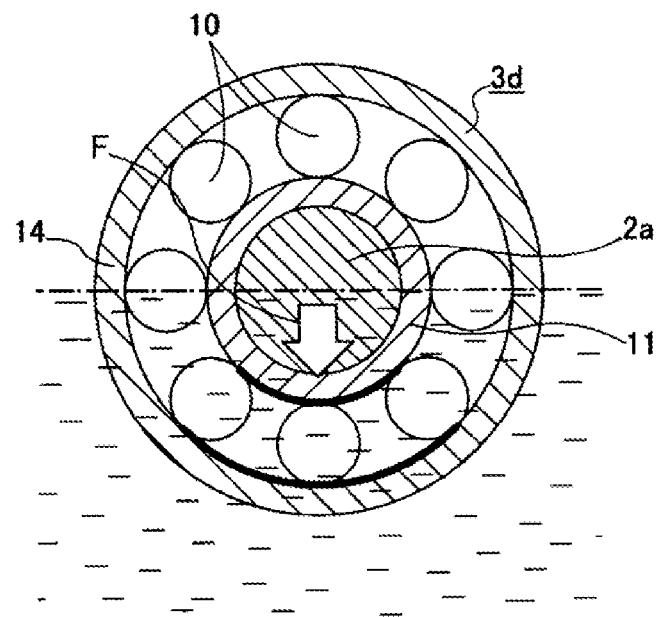
FIG. 4A is a sectional view for describing a problem of applying a radial load in the vertical direction.
Figure 4B:
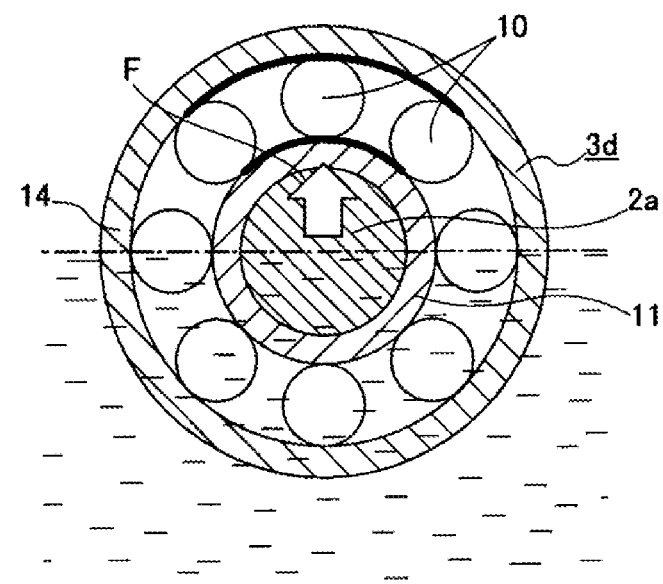
FIG. 4B is another sectional view for describing the problem of applying a radial load in the vertical direction.
Figure 7:
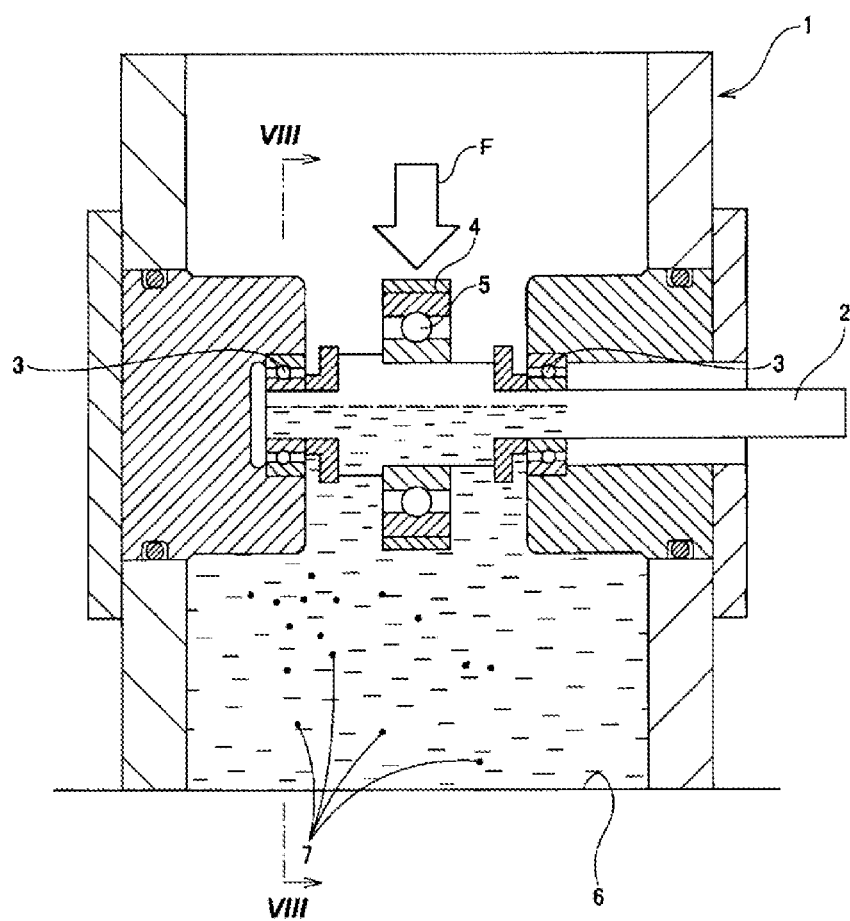
FIG. 7 is a sectional view of a radial rolling-bearing testing device in a first example of the related art.
Figure 8:
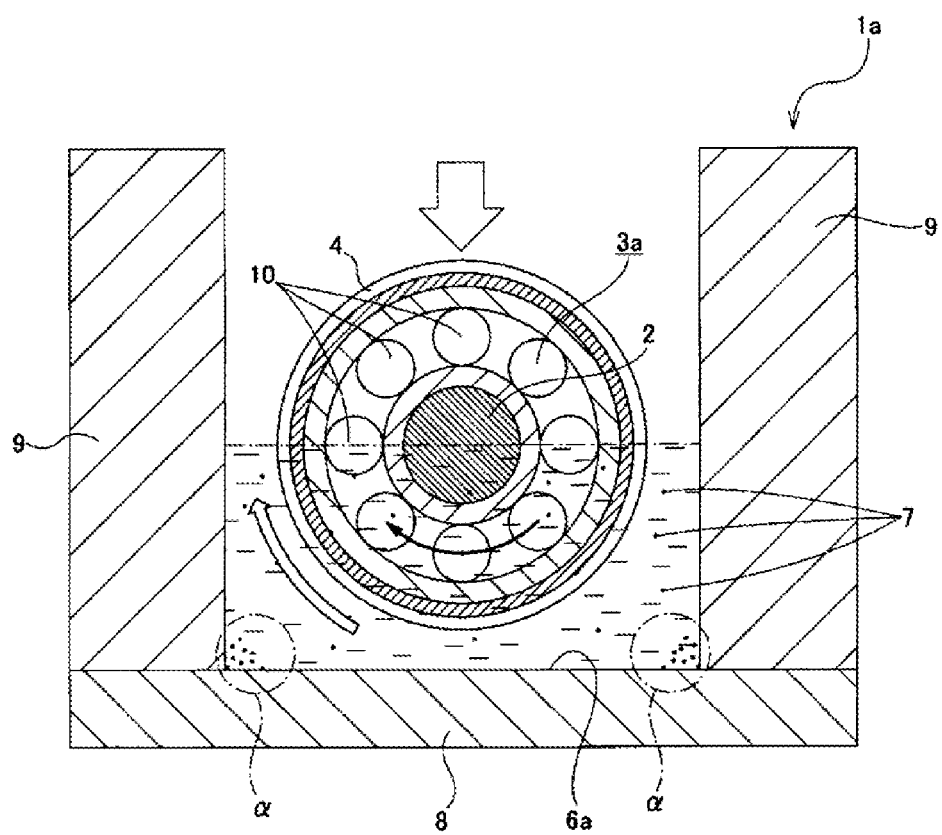
FIG. 8 is a sectional view of a radial rolling-bearing testing device in a second example of the related art which is equivalent to a section along line VIII-VIII in FIG. 7.

The points described above will be described using FIGS. 4A to 5B in addition to FIG. 2. FIG. 4A and FIG. 4B illustrate a structure in which the radial load is applied in the vertical direction to a radial rolling bearing 3d, which is a bearing to be tested, in the same manner as the example of the related art described above. First, in a case where the inner ring 11 of the radial rolling bearing 3d is pressed downward in the vertical direction via the rotary shaft 2a, as shown in FIG. 4A, a lower end section (a portion illustrated by a thick line) of the radial rolling bearing 3d is the load zone. That is, a radial load F is applied to the lower end section. Since the lower half section of the radial rolling bearing 3d is immersed in the lubricant, the lubricant state of the load zone is excessive (excessively enhanced), and the testing time increases. Meanwhile, an upper end section of the support bearing 5 (refer to FIG. 7) becomes the load zone, and the lubricant in the load zone tends to be insufficient or depleted. As a result, a life of the support bearing 5 shortens, and it is necessary to frequently replace the support bearing 5. There is a possibility that the life of the support bearing 5 becomes shorter than the life of the radial rolling bearing 3d, and the life testing of the radial rolling bearing 3d is not normally performed. In contrast to this, in a case where the inner ring 11 of the radial rolling bearing 3d is pressed upward in the vertical direction via the rotary shaft 2a, as shown in FIG. 4B, the upper end section (a portion illustrated by a thick line) of the radial rolling bearing 3d is the load zone. That is, the radial load F is applied to the upper end section. Since the lubricant tends to be insufficient or depleted in the upper end section which becomes the load zone, in a case where the life testing is performed, there is a possibility that the testing results vary greatly due to whether or not splashes of the lubricant splatter on the upper end section of the radial rolling bearing 3d for some reason. Such variation is remarkable in a case where the foreign matters 7 and 7 are mixed into the lubricant.

Figure 5A:
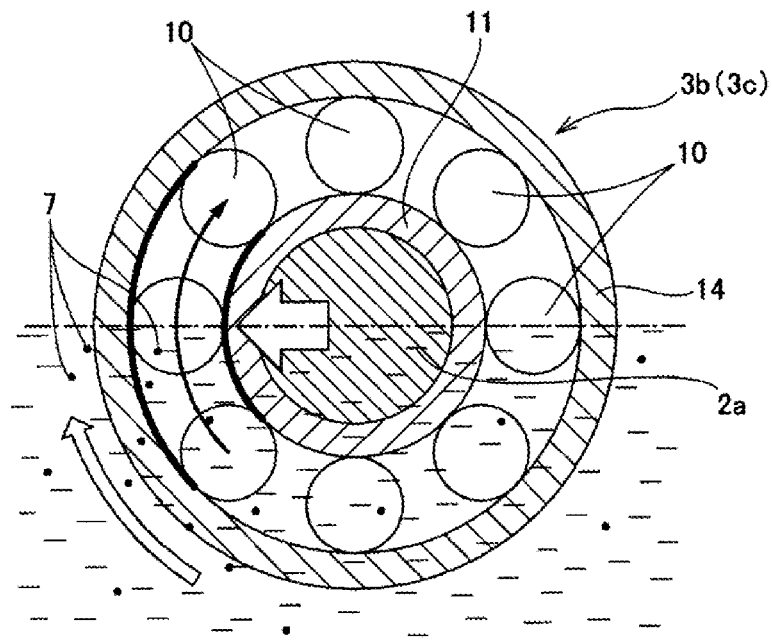
FIG. 5A is a sectional view for describing the effect of regulating the rotary shaft in the rotation direction.
Figure 5B:
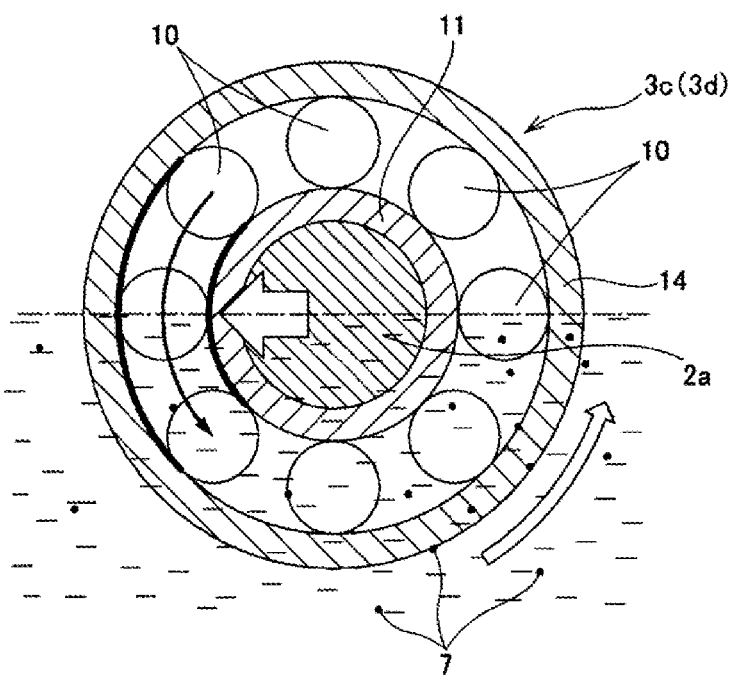
FIG. 5B is another sectional view for describing the effect of regulating the rotary shaft in the rotation direction.

In contrast to this, in a case where the radial load Fr is applied in the horizontal direction to the radial rolling bearings 3b and 3c, and the revolving direction of each ball 10 and 10 is set as a direction which passes the load zone from below to above, as shown in FIG. 5A, it is possible to cause a flow from the bottom section of the lubricant reservoir 6b to the load zone in lubricant oil. As a result, in the load zone, even in a portion which is not immersed in the lubricant, since it is possible to cause a portion of the lubricant to splatter, it is possible to spread the lubricant well, and it is possible to perform the testing stably. It is possible to appropriately feed the foreign matters 7 and 7 which are mixed in the lubricant to the load zone. Meanwhile, in a case where the revolving direction of each of the balls 10 and 10 is set as a direction which passes the load zone from above to below, as shown in FIG. 5B, it is possible to cause a flow facing an opposite side to the load zone in relation to the circumferential direction of the radial rolling bearing 3b (3c) in the lubricant oil. Therefore, in the load zone, the lubricant is insufficient in a portion which is not immersed in the lubricant. Accordingly, in the portion (range) in which the lubricant is insufficient, the lubricant state is varied due to an effect of a slight splash, and the testing results are caused to vary. It is not possible to feed an appropriate amount of the foreign matters 7 and 7 to the load zone (the foreign matters 7 and 7 accumulate at a non-load zone side due to the flow of the lubricant). In the state before the rotary shaft 2a is driven so as to rotate, since the oil level of the lubricant is positioned on the central axis of the rotary shaft 2a, by lubricating an abutting section of the outer peripheral surface of the movable housing 4a and the leading end surface of the pressing jig 22, it is possible to prevent a generation of fretting between the surfaces. Furthermore, since at least a lower end section of the outer peripheral surface of the rotary shaft 2a is immersed in the lubricant, it is possible to suppress a temperature variance of a member, which is disposed inside the fixed housing 1b, such as the radial rolling bearings 3b and 3c, and the rotary shaft 2a.

Furthermore, in the case of the present example, since the entirety of the fixed housing 1b is integrally formed, it is possible to increase a rigidity with respect to the radial load Fr and the axial load Fa. This point will be described using FIG. 6 which illustrates a structure according to a comparative example in addition to FIG. 2. In the same manner as the case of the second example of the related art described above, in the fixed housing 1c with a rectangular box form which is open upward, a pair of side plate sections 9a and 9a which are parallel to each other, and a pair of end plate sections which each connect end sections of the side plate sections 9a and 9a are formed so as to be respectively supportedly fixed to end plate section 8a with a flat plate form by welds and the like. That is, the fixed housing 1b is formed such that five plate members are connected. For this reason, in a case where the radial load Fr which is applied to the rotary shaft 2a in the horizontal direction is increased, there is a possibility that the side plate section 9a (the left side in FIG. 6) of the fixed housing 1c which supports the radial load Fr deforms in a direction that falls toward a direction in which the radial load Fr applies. As a result, there is a possibility that a variance of testing results is increased since it is not possible to normally apply the radial load Fr to the radial rolling bearings 3b and 3c. In contrast to this, in the case of the present example, since the entirety of the fixed housing 1b is integrally formed, and the rigidity with respect to the radial load Fr is increased, it is possible to prevent a variance of testing results by normally applying the radial load Fr to the radial rolling bearings 3b and 3c. Furthermore, since the fixed housing 1b is integrally formed, the bottom surface of the lubricant reservoir 6b is set as the curved concave surface, and plate thicknesses of the width direction side wall sections 20a and 20b are larger at the lower end side than the upper end, it is possible to further increase a rigidity with respect to the radial load Fr. Since there are no joints formed by combining a plurality of plate members on the inside surface of the lubricant reservoir 6b, it is possible to enhance an heat transferability. Furthermore, when the inside of the lubricant reservoir 6b is cleaned, the foreign matters 7 and 7 are not stagnated in the joint by adhesion (catching). Also from this perspective, it is possible to suppress a variation of testing results by uniformly maintaining properties of the lubricant.

Furthermore, in the case of the present example, the vibration sensor 26 is installed on the pressing plate 25 which is provided between a base end surface of the pressing jig 22 of which a leading end surface abuts against the movable housing 4a, and the steel ball 24 which is pressed by the pressing rod 23. That is, since the vibration sensor 26 is provided so as to detect a vibration of the pressing plate 25 which is provided in series to the direction in which the radial load Fr applies, it is possible to secure a detection precision of a vibration of the radial rolling bearings 3b and 3c. In addition, the base end surface of the pressing jig 22 is caused to be in surface contact with the pressing plate 25. Also from this perspective, it is possible to achieve an improved detection precision of the vibration. Since the vibration sensor 26 is provided outside the fixed housing 1b, it is possible to prevent splashes of the lubricant from splattering on the vibration sensor 26, and the temperature from becoming high due to generation of heat in the heater 27.

Example of Embodiment

Next, an experiment which is performed in order to confirm effects of the embodiment of the present invention will be described. In the experiment, a life testing for durability evaluation testing is performed ten times in one cycle in a target of examples in which the testing device and the rotation directions of the rotary shaft are different, and a variance of testing results is inspected. An example of the embodiment and a comparative example 1 use the testing device according to the embodiment described above, and a comparative example 2 uses the testing device illustrated in FIG. 6. Conditions of the life testing are as follows. The rotation direction of the rotary shaft is set as a direction such that the rolling element of the bearing to be tested passes the load zone from below to above in the example of the embodiment and the comparative example 2, and is set as a direction such that the rolling element passes the load zone from above to below in comparative example 1.

Bearing to be tested: bearing number 6208 (outer diameter=80 mm, inner diameter=40 mm, width=18 mm)

Testing load: 7300 N {P/C (applied load/rated load)=0.25}

Rotation speed: 4500 min$^{-1}$

Testing temperature: 100° C.

Lubricant: transmission oil

Foreign matters: predetermined amount of mixed iron-based metal powders

Under such conditions, a point in time, when a vibration value of the tested bearing which is detected by the vibration sensor is set 2 times an initial vibration value, is set as a life of the bearing to be tested. Then, the testing stops at that point in time, and a presence or absence of a separation of the inner ring raceway, the outer ring raceway, and a rolling contact surface of each rolling element is visually confirmed. The longest testing time is set as 500 hours (Hr), and in relation to the bearing to be tested in which the vibration value reaches two times the initial vibration value at a point in time in which 500 hours have elapsed, a subsequent testing is stopped. The results of the life testing are shown in table 1.

and an elastic deformation is generated in the side plate section of the fixed housing, it is not possible to normally apply the radial load to the bearing to be tested. In the case of the comparative example 2, since the radial load is not normally applied to the bearing to be tested, and it is not possible to sufficiently supply foreign matters to the bearing to be tested, a stop time is exceeded in 40% of the bearings to be tested. In contrast to this, in the case of the example of the embodiment, a difference between a maximum value and a minimum value of the life is small at 1.6 times, and the value of a weibull slope is high at 6.3. The damaged part is the inner ring or the inner and outer rings.

The present invention is based on Japanese Patent Applications No. 2013-079789 filed on Apr. 5, 2013 and Japanese Patent Application No. 2013-079790 filed on Apr. 5, 2013, the contents of which are incorporated herein by reference.

REFERENCE SIGNS LIST 1, 1a to 1c FIXED HOUSING
2, 2a ROTARY SHAFT
3, 3a to 3d RADIAL ROLLING BEARING
6, 6a, 6b LUBRICANT RESERVOIR
7 FOREIGN MATTER
10 BALL
11 INNER RING
14 OUTER RING
17a, 17b SUPPORT SLEEVE
22 PRESSING JIG
23 PRESSING ROD

TABLE 1

| | Example of Embodiment | | Comparative Example 1 | | Comparative Example 2 | |
| --- | --- | --- | --- | --- | --- | --- |
| | Life | Damaged Part | Life | Damaged Part | Life | Damaged Part |
| 1 | 152 Hr | Inner and Outer Rings | 232 Hr | Inner Ring | 500 Hr | Stopped |
| 2 | 109 Hr | Inner Ring | 348 Hr | Inner Ring | 421 Hr | Inner Ring |
| 3 | 130 Hr | Inner Ring | 155 Hr | Ball | 500 Hr | Stopped |
| 4 | 126 Hr | Inner Ring | 206 Hr | Outer Ring | 500 Hr | Stopped |
| 5 | 99 Hr | Inner Ring | 75 Hr | Inner Ring | 368 Hr | Inner Ring |
| 6 | 115 Hr | Inner Ring | 95 Hr | Inner Ring | 101 Hr | Inner Ring |
| 7 | 108 Hr | Inner Ring | 320 Hr | Inner and Outer Rings | 440 Hr | Inner Ring |
| 8 | 148 Hr | Inner and Outer Rings | 125 Hr | Inner Ring | 192 Hr | Inner Ring |
| 9 | 95 Hr | Inner Ring | 62 Hr | Inner Ring | 71 Hr | Inner Ring |
| 10 | 101 Hr | Inner Ring | 254 Hr | Inner Ring | 500 Hr | stopped |
| $L_{10}$ Life | 88.9 Hr | | 61.9 Hr | | 81.9 Hr | |
| $L_{50}$ Life | 119 Hr | | 175 Hr | | 450.2 Hr | |
| Weibull Slope | 6.3 | | 1.8 | | 1.1 | |

As understood from table 1, it is possible to suppress a variance of the testing results in the embodiment in comparison to the comparative examples 1 to 2. That is, in a case of the comparative example 1, since the lubricant is insufficient in a portion which is not immersed in the lubricant in the load zone, and it is not possible to sufficiently supply foreign matters to the bearing to be tested, a difference between a maximum value and a minimum value of the life is 5 times or more, and a value of a weibull slope is low at 1.8. Furthermore, in every each of the bearings to be tested, any of the inner ring, the outer ring, and the ball are damaged, and the variance of the damaged part is also generated. In the case of the comparative example 2, since the rigidity of the fixed housing is insufficient with respect to the radial load which is applied in the horizontal direction,

24 STEEL BALL
25 PRESSING PLATE
27 HEATER

The invention claimed is:

1. A radial rolling-bearing testing device for performing a testing of a bearing life of a radial rolling bearing which includes an outer ring that has an inner peripheral surface on which an outer ring raceway is formed, an inner ring that has an outer peripheral surface on which an inner ring raceway is formed, and a plurality of rolling elements which are provided so as to freely rotate between the outer ring raceway and the inner ring raceway, the device comprising:

a rotary shaft which the inner ring of the radial rolling bearing is fitted outside;

a rotational driving section which is configured so as to rotate the rotary shaft;

a lubricant reservoir which is configured so as to retain lubricant in which a portion of the radial rolling bearing is immersed;

a load applying section which is configured so as to apply a radial load to the radial rolling bearing;

a heater which is configured so as to maintain an oil temperature of the lubricant at a desired temperature; and a support sleeve which the radial rolling bearing is fitted inside, wherein a bottom surface of the lubricant reservoir is a curved concave surface with a partial cylindrical form which is concentric to a central axis of the rotary shaft and the heater is provided between the bottom surface of the lubricant reservoir and an outer peripheral surface of the support sleeve, and a gap is interposed between a lower surface of the heater and a bottom surface of the lubricant reservoir, and between a upper surface of the heater and the outer peripheral surface of the support sleeve.

2. The radial rolling-bearing testing device according to claim 1, wherein a radius of a curvature of the bottom surface of the lubricant reservoir is 0.6 times or more and 2 times or less than an outer diameter of the radial rolling bearing.

3. The radial rolling-bearing testing device according to claim 1, wherein in a state before the rotary shaft is driven so as to rotate, an oil level of the lubricant is positioned on a central axis of the rotary shaft.

4. The radial rolling-bearing testing device according to claim 1, wherein the heater is curved along the bottom surface of the lubricant reservoir.

5. The radial rolling-bearing testing device according to claim 1, wherein a foreign matter is mixed into the lubricant.

6. The radial rolling-bearing testing device according to claim 1, wherein the load applying section applies the radial load in a horizontal direction.

7. The radial rolling-bearing testing device according to claim 1, the device further comprising a housing;

wherein the rotary shaft is rotatably supported inside the housing and an entirety of the housing is integrally formed.

8. The radial rolling-bearing testing device according to claim 7, wherein the housing is a carbon steel.

* * * * *